United States Patent
Ketelson et al.

(10) Patent No.: US 7,344,725 B2
(45) Date of Patent: Mar. 18, 2008

(54) USE OF INORGANIC NANOPARTICLES TO STABILIZE HYDROGEN PEROXIDE SOLUTIONS

(75) Inventors: Howard Allen Ketelson, Fort Worth, TX (US); Nathaniel D. McQueen, Arlington, TX (US)

(73) Assignee: Alcon, Inc., Hunenberg (CH)

( * ) Notice: Subject to any disclaimer, the term of this patent is extended or adjusted under 35 U.S.C. 154(b) by 149 days.

(21) Appl. No.: 10/989,630

(22) Filed: Nov. 16, 2004

(65) Prior Publication Data

US 2005/0129782 A1    Jun. 16, 2005

Related U.S. Application Data

(60) Provisional application No. 60/524,942, filed on Nov. 25, 2003.

(51) Int. Cl.
*A61K 9/00*    (2006.01)
*A61K 9/14*    (2006.01)

(52) U.S. Cl. .............. 424/400; 424/489; 424/616; 514/912; 514/915

(58) Field of Classification Search ............. 424/400, 424/489, 616; 514/912, 915
See application file for complete search history.

(56) References Cited

U.S. PATENT DOCUMENTS 5,725,887 A * 3/1998 Martin et al. .............. 424/613

6,106,812 A   8/2000 Prencipe et al.
6,165,415 A   12/2000 Hunt et al.
2004/0241206 A1 * 12/2004 Ketelson et al. ............ 424/429

FOREIGN PATENT DOCUMENTS

| GB | 2 245 605 | | 1/1992 |
| GB | 2 245 605 A | * | 1/1992 |
| WO | WO 03/059193 | | 7/2003 |

OTHER PUBLICATIONS

Gieseking; *The Mechanism of Cation Exchange in the Montmorillonite-Beidellite-Nontronite Type of Clay Materials*; Soil Science; vol. 47; p. 1-14; 1939.

* cited by examiner

*Primary Examiner*—Sreeni Padmanabhan
*Assistant Examiner*—Konata M. George
(74) *Attorney, Agent, or Firm*—Mark E. Flanigan

(57) ABSTRACT

The use of inorganic nanoparticles to stabilize aqueous hydrogen peroxide solutions is described. The preferred nanoparticles are formed from clays. The use of nanoparticles formed from synthetic smectite clays is particularly preferred. The stabilized hydrogen peroxide solutions may be utilized for various purposes, but are particularly useful as contact lens disinfecting solutions.

10 Claims, No Drawings

USE OF INORGANIC NANOPARTICLES TO STABILIZE HYDROGEN PEROXIDE SOLUTIONS

CLAIM FOR PRIORITY

This application claims priority from U.S. Patent Application Ser. No. 60/524,942, filed Nov. 25, 2003.

BACKGROUND OF THE INVENTION

The present invention is directed to a new method for stabilizing hydrogen peroxide solutions. The invention is particularly directed to the provision of various types of pharmaceutical compositions containing stabilized hydrogen peroxide at relatively low concentrations, such as ophthalmic, otic, nasal and dermatological compositions. The invention is especially useful in the fields of hydrogen peroxide solutions for disinfecting contact lenses and ophthalmic compositions that contain very low concentrations of hydrogen peroxide as an antimicrobial preservative.

Hydrogen peroxide is inherently unstable in aqueous solutions due to its susceptibility to decomposition by trace levels of transition metal ions in solution. These ions serve as catalysts to the decomposition of hydrogen peroxide into oxygen and water.

In order to address this stability problem, it is necessary to include a stabilizing agent in hydrogen peroxide solutions. Examples of such stabilizing agents include: phosphonates, such as those sold under the name "DEQUEST" (a trademark of Monsanto); sodium thiosulfate; and sodium stannate. The use of phosphonates to stabilize hydrogen peroxide in ophthalmic compositions is described in U.S. Pat. No. 5,725,887.

The use of inorganic nanoparticles as carriers for biocides in ophthalmic compositions is described in International (PCT) Publication No. WO 03/059193.

SUMMARY OF THE INVENTION

The present invention is directed to a new method for stabilizing hydrogen peroxide solutions. The method is based on the discovery that inorganic nanoparticles can minimize the decomposition of hydrogen peroxide in aqueous solutions.

Not wishing to be bound by theory, it is believed that the nanoparticles sequester the metal ions through ionic attractions between the negatively charged region of the surface of the nanoparticles and the positive charge on the metal ions. This interaction is believed to effectively prevent the metal ion from catalyzing the decomposition of hydrogen peroxide.

The stabilization method of the present invention has several advantages over prior methods. For example, the inorganic nanoparticles do not cause staining or other adverse effects when used in ophthalmic compositions. In contrast, the use of sodium stannate to stabilize hydrogen peroxide solutions for disinfecting contact lenses is known to cause staining of some types of lenses, and the use of sodium thiosulfate produces an unpleasant odor. The nanoparticles also have positive effects apart from the stabilization of the hydrogen peroxide, such as enhancement of the lubricity of the solutions.

DETAILED DESCRIPTION OF THE INVENTION

The nanoparticles utilized in the present invention are formed from inorganic materials. The particles have colloidal dimensions, a large surface area and a high ion exchange capacity. The particles are generally referred to hereinafter as "inorganic nanoparticles". The use of synthetic inorganic nanoparticles is preferred.

The nanoparticles used in the present invention preferably have particle dimensions less than 100 nanometers ("nm"), but greater than 1 nm. The morphology of the nanoparticles is not limited to being spherical; plate-like, cubic, ellipsoid or other particle shapes are also useful. The particles have surface areas ranging from 30-1000 square meters/gram ("$m^2/g$"), and have an overall negative surface charge at a pH in the range of 6.0-7.8. The particles display Newtonian viscosity behavior in the concentration ranges described herein.

The inorganic nanoparticles may also be surface modified depending on the application and stability requirements. Different types of nanoparticles may be combined to optimize the formulation properties.

The inorganic nanoparticles utilized in the present invention are preferably formed from clays that swell in aqueous solutions. These types of clays are referred to herein as being "hydrous". The use of nanoparticles of synthetic hydrous clays is preferred due to the commercial availability, purity, and well-defined chemical composition and physical properties of these materials. In addition, the synthetic clay nanoparticles are easier to formulate and can form colorless and transparent gels more readily than inorganic nanoparticles formed from naturally occurring clays.

Synthetic inorganic nanoparticles that are particularly useful include a synthetic smectite clay that is commercially available under the trademark Laponite® (Southern Clay Products, Gonzales, Tex., USA). Laponite® is a layered hydrous magnesium silicate prepared from simple silicates. The following publication may be referred to for further details concerning the physical properties and functions of Laponite®: "Laponite Technical Bulletin "Laponite-synthetic layered silicate—its chemistry, structure and relationship to natural clays" L204/01g. Another synthetic magnesium aluminum silicate material is also commercially available under the trademark OPTIGEL® SH (Sud-Chemie, Louisville, Ky.).

Inorganic nanoparticles formed from naturally occurring hydrous clays may also be utilized, either in combination with a synthetic clay or alone. Examples of suitable naturally occurring clays include aliettite, beidellite, bentonite, hectorite, kaolinite, magadite, montmorillonite, nontronite, saponite, sauconite, stevensite and volkonskoite.

The following publications may be referred to for further details regarding the physical properties of various types of clay nanoparticles and the use of these materials as ion-exchange materials, viscosity modifiers and film forming agents:

Gieseking, J. E., "Mechanism of Cation Exchange in the Mont-Morillonite-Beidellite-Nontronite Type of Clay Minerals", *Soil Science*, volume 47, pages 1-14 (1939);

Theng, B. K. G., "Formation and Properties of Clay-Polymer Complexes", Elsevier, Amsterdam, (1979); and H. van Olphen, "Clay Colloid Chemistry", Krieger Publishing Company, Florida, Second Edition (1991).

Examples of other inorganic nanoparticle materials that may be utilized instead of or in combination with the clay nanoparticles described above include zeolites, silica, aluminum oxide, cerium oxide, titanium oxide and zinc oxide. Nanometer sized silica particles, such as those supplied by Nalco (e.g., Nalco® 115 and 1140) and EKA Chemicals (NYACOL® grades), are readily available. Mineral oxide nanoparticles based on other metals are also commercially available. For example, mineral oxides (e.g., aluminum oxide, cerium oxide, titanium oxide and zinc oxide) having well defined nano-dimensions are available from Nanophase Technologies (Romeoville, Ill., USA) under the trade name "NanoTek®".

The amount of nanoparticles required to stabilize a particular hydrogen peroxide solution will vary depending on factors apparent to those skilled in the art, such as the type of nanoparticle selected, the concentration of hydrogen peroxide in the solution, the degree of stabilization desired, the presence or absence of other components in the solution that may affect hydrogen peroxide stability, and the intended use or function of the hydrogen peroxide in the solution (e.g., topical antiseptic, contact lens disinfection, or prevention of microbial contamination). The concentration of nanoparticles required to achieve stabilization of hydrogen peroxide is referred to herein as "a stabilizing effective amount". The concentration will typically be on the order of 50 parts per million or higher.

The present invention is not limited relative to the types of hydrogen peroxide compositions that may be stabilized by means of the present invention. Examples of the types of compositions that may be stabilized include: concentrated solutions utilized in industrial or laboratory applications; compositions utilized as topical antiseptics on the skin or other tissues; solutions for disinfecting contact lenses; and various types of pharmaceutical compositions wherein the hydrogen peroxide is functioning as an antimicrobial preservative, such as the ophthalmic compositions described in U.S. Pat. No. 5,725,887 (Martin, et al.), the entire contents of which are hereby incorporated in the present specification by reference.

The following examples are presented to further illustrate the invention:

EXAMPLE 1

3% hydrogen peroxide solutions containing three different stabilizing agents were formulated in phosphate buffer at pH 6.5. 10 ml samples were heated in HCl-cleaned test tubes at 100° C. for 24 hours to simulate a two year shelf life. Then a 200 microliter aliquot was added to 40 ml of a 2.75% $H_2SO_4$ solution and titrated with 0.01N $KMnO_4$. This result was compared with a non-heated sample (i.e., 25° C.) to obtain the percentage stability of $H_2O_2$. The results are presented in Table 1, below:

TABLE 1

| Test Compound | Temperature (° C.) | $KMnO_4$ (mL) Used | % Stability of $H_2O_2$ |
|---|---|---|---|
| Laponite ® XLG, 10 ppm | 25 | 38.6 | 90.2 |
| | 100 | 34.8 | |
| Laponite ® XLG, 50 ppm | 25 | 39.8 | 99.0 |
| | 100 | 39.4 | |
| Laponite ® XLG, 100 ppm | 25 | 39.0 | 100 |
| | 100 | 39.0 | |
| Laponite ® XLG, 100 ppm | 25 | 40.9 | 99.7 |
| | 100 | 40.8 | |
| EDTA, 500 ppm | 25 | 43.1 | 24.8 |
| | 100 | 10.7 | |
| Dequest ® 2060, 180 ppm | 25 | 62.8 | 98.2 |
| | 100 | 61.7 | |

Conclusion

Laponite® XLG exhibits remarkable hydrogen peroxide stability under these conditions (phosphate buffer, no salt, pH 6.5). 50 ppm Laponite shows better stability than Dequest® 2060, a commercial stabilizer used in lens care products containing 3% hydrogen peroxide (i.e., CIBA Vision's AOSEPT® Disinfecting Solution).

EXAMPLE 2

50 ppm Laponite® XLG was formulated in phosphate buffer at four different pH levels and four different concentrations of $H_2O_2$. 10 ml samples were heated in HCl-cleaned test tubes at 100° C. for 24 hours to simulate a two year shelf life. Then an aliquot was added to 40 ml of a 2.75% $H_2SO_4$ solution and titrated with $KMnO_4$. The amounts of the aliquot and the $KMnO_4$ varied with the concentration of the $H_2O_2$. This result was compared with a non-heated sample to obtain the percentage stability of $H_2O_2$. The results are shown in Table 2, below:

TABLE 2

| Concentration of hydrogen peroxide | pH | Temperature (° C.) | $KMnO_4$ (mL) Used | % Stability of $H_2O_2$ |
|---|---|---|---|---|
| 3.0% | 6.5 | 25 | 43.3 | 96.3 |
| | | 100 | 41.7 | |
| 3.0% | 7.0 | 25 | 43.7 | 95.2 |
| | | 100 | 41.6 | |
| 3.0% | 8.0 | 25 | 43.3 | 86.1 |
| | | 100 | 37.3 | |
| 3.0% | 9.0 | 25 | 43.0 | 46.5 |
| | | 100 | 20.0 | |
| 1.0% | 6.5 | 25 | 30.9 | 93.2 |
| | | 100 | 28.8 | |
| 0.1 | 6.5 | 25 | 27.7 | 97.8 |
| | | 100 | 27.1 | |
| 0.01 | 6.5 | 25 | 6.5 | 95.4 |
| | | 100 | 6.2 | |

Conclusion

Laponite® XLG exhibits remarkable hydrogen peroxide stability over a broad range of hydrogen peroxide concentrations. However, as would be expected, its stabilizing effectiveness decreases with an increase in pH, due to the inherent instability of hydrogen peroxide at alkaline pH levels.

EXAMPLE 3

The effectiveness of 50 ppm Laponite® XLG to stabilize 100 ppm $H_2O_2$ at various pH levels was evaluated.

50 ppm Laponite® XLG was formulated in a phosphate buffer (0.8655% NaCl, 0.0622% sodium phosphate dibasic, 0.0072% sodium phosphate monobasic monohydrate), along with 100 ppm hydrogen peroxide (from a 30% unstabilized solution). 100 mL samples were then adjusted to pH levels of 6.5, 7.0 and 7.5, respectively. 10 mL of each sample was then placed in a test tube, sealed with a screw cap, and heated to 100° C. for 24 hours. After heating, 5 mL of each sample was titrated with 0.002% $KMnO_4$ and compared to the unheated sample to obtain % stability. 60 ppm of Dequest® 2060 at pH 6.5 was used as a control. Table 3 below contains the results of this experiment:

TABLE 3

Stability of 100 ppm $H_2O_2$ at various pHs in presence of 50 ppm Laponite ® XLG

| pH | mL 0.002 $H_2O_2$ RT | 100° C. | % stability |
|---|---|---|---|
| 6.5 | 20.1 | 18.0 | 89.6 |
| 7.0 | 20.5 | 18.7 | 91.2 |
| 7.5 | 20.5 | 19.0 | 92.7 |
| 60 ppm Dequest ® 2060 (control) | 21.0 | 19.5 | 92.9 |

Conclusion

The stability of 100 ppm hydrogen peroxide in the presence of 50 ppm Laponite® XLG is comparable to the stabilization achieved with 60 ppm of Dequest® 2060. Also, there did not appear to be a pH effect on the stability.

EXAMPLE 4

The antimicrobial activity of several hydrogen peroxide solutions was evaluated using standard microbiological testing procedures. The composition of the solutions is shown in Table 4 below. Solutions 83A and 83B were stabilized with inorganic nanoparticles (i.e., Laponite® XLG), in accordance with the present invention. Solutions 83C and 83D were stabilized with a phosphonate (i.e., Dequest® 2060), as described in U.S. Pat. No. 5,725,887. Solutions 83E and 83F did not contain a stabilizing agent, but were otherwise identical to the preceding solutions. A commercial hydrogen peroxide solution utilized for the disinfection of contact lenses (i.e., CIBA Vision's Product AOSEPT®) was utilized as a reference standard.

The solutions were tested in 50 ml polystyrene centrifuge tubes. A platinum-coated disk (i.e., AODISC® Neutralizer) was added to the tubes immediately following inoculation with the respective microbes.

As demonstrated by the results presented in Table 4, the solutions of the present invention exhibited a level of antimicrobial activity that was comparable to that of Solutions 83C-83F and superior to that of the commercially available hydrogen peroxide disinfecting solution. These results demonstrate that the use of inorganic nanoparticles to stabilize hydrogen peroxide solutions does not adversely affect the antimicrobial activity of the solutions.

TABLE 4

| | Concentration (% w/v) | | | | | | |
|---|---|---|---|---|---|---|---|
| Component | 10509-83A | 10509-83B | 10509-83C | 10509-83D | 10509-83E | 10509-83F | AOSEPT ®[a] |
| Hydrogen peroxide | 0.01 | 3.0 | 0.01 | 3.0 | 0.01 | 3.0 | |
| Laponite ® XLG | 0.0025 | 0.0025 | | | | | |
| Dequest ® 2060 | | | 0.006 | 0.006 | | | |
| Boric acid | 0.6 | 0.6 | 0.6 | 0.6 | 0.6 | 0.6 | |
| Sodium citrate | 0.6 | 0.6 | 0.6 | 0.6 | 0.6 | 0.6 | |
| Propylene glycol | 0.5 | 0.5 | 0.5 | 0.5 | 0.5 | 0.5 | |
| Tetronic 1304 | 0.1 | 0.1 | 0.1 | 0.1 | 0.1 | 0.1 | |
| Tricine | 0.2 | 0.2 | 0.2 | 0.2 | 0.2 | 0.2 | |
| pH | 7.0 | 7.0 | 7.0 | 7.0 | 7.0 | 7.0 | |

| | Time | $Log_{10}$ Reduction of Survivors | | | | | | |
|---|---|---|---|---|---|---|---|---|
| Microorganism | (hrs) | 10509-83A | 10509-83B | 10509-83C | 10509-83D | 10509-83E | 10509-83F | AOSEPT ® |
| _C. albicans_ | 1 | 0.0 | _6.1_ | 0.0 | _6.1_ | 0.0 | 5.1 | 2.6 |
| $1.2 \times 10^b$ | 6 | 0.4 | _6.1_ | 0.2 | _6.1_ | 0.3 | _6.1_ | 3.4 |
| | 24 | 0.9 | _6.1_ | 0.1 | _6.1_ | 0.4 | _6.1_ | 3.8 |
| _P. aeruginosa_ | 1 | 1.3 | _6.0_ | 2.4 | _6.0_ | 1.4 | _6.0_ | _6.0_ |
| $1.0 \times 10^6$ | 6 | 5.3 | _6.0_ | _6.0_ | _6.0_ | _6.0_ | _6.0_ | _6.0_ |
| | 24 | _6.0_[c] | _6.0_ | _6.0_ | _6.0_ | _6.0_ | _6.0_ | _6.0_ |
| _S. marcescens_ | 1 | 0.0 | _6.1_ | 0.1 | 4.3 | 0.1 | _6.1_ | 3.5 |
| $1.2 \times 10^6$ | 6 | 0.3 | _6.1_ | 0.2 | _6.1_ | 0.2 | _6.1_ | 4.8 |
| | 24 | 1.0 | _6.1_ | 1.4 | _6.1_ | 1.2 | _6.1_ | _6.1_ |
| | | | | | | | | 11239:029 |

[a]CIBA Vision ® AOSEPT ® Disinfecting Solution, lot 26214, exp. 09/2005
[b]Inoculum control count
[c]Underlined number indicates no survivors (<10 CFU/mL) recovered

We claim:

1. In an aqueous hydrogen peroxide solution that is suitable for disinfecting contact lenses and, has a pH in the range of 6.5 to 7.5, the improvement which comprises including in said solution an amount of inorganic nanoparticles effective to stabilize the hydrogen peroxide.

2. An improved hydrogen peroxide contact lens disinfecting solution of claim 1, wherein the hydrogen peroxide concentration is 3%.

3. An improved hydrogen peroxide contact lens disinfecting solution of claim 1, wherein the inclusion of the inorganic nanoparticles in said solution also enhances the lubricity of the solution.

4. An improved hydrogen peroxide contact lens disinfecting solution of claim 3, wherein the hydrogen peroxide concentration is 3%.

5. An improved hydrogen peroxide contact lens disinfecting solution of claim 1, wherein the inorganic nanoparticles are formed from a synthetic smectite clay.

6. An improved hydrogen peroxide solution of claim 1, wherein the nanoparticles have a surface area ranging from 30 to 1,000 $m^2/g$.

7. A method of disinfecting a contact lens which comprises treating the lens with an aqueous hydrogen peroxide solution containing an amount of inorganic nanoparticles effective to stabilize the hydrogen peroxide in the solution.

8. A method of according to claim 7, wherein treating the lens with said solution does not result in staining of the lens.

9. A method of according to claim 8, wherein the inorganic nanoparticles enhance the lubricity of said solution, and treating the lens with said solution lubricates the lens.

10. A method of according to claim 8, wherein treating the lens with said solution does not produce an unpleasant odor.

* * * * *